(12) United States Patent
Lee et al.

(10) Patent No.: US 7,718,803 B2
(45) Date of Patent: May 18, 2010

(54) SELF-DISPERSIBLE BIPYRIDINE-BASED METAL COMPLEX AND INK COMPOSITION COMPRISING THE SAME

(75) Inventors: Jong-in Lee, Suwon-si (KR); Seung-min Ryu, Yongin-si (KR); Su-aa Jung, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 370 days.

(21) Appl. No.: 10/896,029

(22) Filed: Jul. 22, 2004

(65) Prior Publication Data

US 2005/0033040 A1 Feb. 10, 2005

(30) Foreign Application Priority Data

Aug. 8, 2003 (KR) .................. 10-2003-0055023

(51) Int. Cl.
*C07D 471/04* (2006.01)
*C07F 15/00* (2006.01)
*C09D 11/00* (2006.01)

(52) U.S. Cl. .................. 546/10; 546/88; 106/31.47
(58) Field of Classification Search .................. 546/2, 546/10; 106/31.47
See application file for complete search history.

(56) References Cited

U.S. PATENT DOCUMENTS

| | | | |
|---|---|---|---|
| 3,971,739 A | 7/1976 | McCrae et al. | |
| 3,987,023 A | 10/1976 | McCrae et al. | |
| 4,077,953 A | 3/1978 | McCrae et al. | |
| 4,152,324 A | 5/1979 | McCrae et al. | |
| 4,611,890 A | 9/1986 | Elliott et al. | |
| 5,100,885 A | 3/1992 | Abrams et al. | |
| 5,104,988 A * | 4/1992 | Ohkawa | 546/2 |
| 5,118,405 A * | 6/1992 | Kaneko et al. | 204/433 |
| 5,393,903 A | 2/1995 | Gratzel et al. | |
| 5,463,057 A * | 10/1995 | Graetzel et al. | 546/4 |
| 5,789,592 A * | 8/1998 | Gratzel et al. | 546/21 |
| 6,028,265 A * | 2/2000 | Ono et al. | 136/263 |
| 6,278,056 B1 * | 8/2001 | Sugihara et al. | 136/263 |
| 6,306,661 B1 * | 10/2001 | Lakowicz et al. | 436/138 |
| 6,403,294 B2 * | 6/2002 | Sato | 430/567 |
| 6,808,939 B2 * | 10/2004 | Sigal et al. | 436/546 |
| 7,019,138 B2 * | 3/2006 | Elliott et al. | 546/2 |
| 2005/0033053 A1 * | 2/2005 | Lee et al. | 546/2 |
| 2005/0119368 A1 * | 6/2005 | Hall-Goulle et al. | 523/160 |
| 2005/0274281 A1 * | 12/2005 | Jackson | 106/31.43 |

FOREIGN PATENT DOCUMENTS

| | | |
|---|---|---|
| JP | 03-050291 | 3/1991 |
| JP | 3-81264 | 4/1991 |
| JP | 04-334393 | 11/1992 |
| JP | 05-097809 | 4/1993 |
| JP | 2001-152044 | 6/2001 |
| JP | 2002-275182 | 9/2002 |

OTHER PUBLICATIONS

Garcia-Fresnadillo et al., Chemical Abstracts, 136:124021, 2001.*
Hara et al., Chemical Abstracts, 136:224079, 2001.*
Sakaki et al., Chemical Abstracts, 137:203849, 2002.*
Schwarz et al., Chemical Abstracts, 132:350181, 2000.*
Srikanth et al., Chemical Abstracts, 138:114902, 2002.*
Margiotta et al., European Journal of Inorganic Chemistry, 6, 1136-1144, published on the web Mar. 3, 2003.*
Office Action of corresponding Korean Patent Application No. 10-2003-005023, dated Aug. 26, 2005 and English translation thereof.
Synthesis, structure and properties of ternary copper(II) complexes of ONO donor Schiff base, imidazole, 2,2'-bipyridine and „10-phenanthroline; Polyhedron, vol. 25, Issue 17, Dec. 4, 2006, pp. 3312-3318, R.N. Patel, Nripendra Singh and V.L.N. Gundla.
Chiral zinc(II) bipyridine complex. Crystal structure and catalytic activity in asymmetric allylation reaction, New J. Chem., 1999, 23, 629-632, Hoi-Lun Kwong, Wing-Tak Wong.

* cited by examiner

*Primary Examiner*—Fiona T Powers
(74) *Attorney, Agent, or Firm*—Staas & Halsey LLP

(57) ABSTRACT

A self-dispersible bipyridine-based metal complex includes a bipyridine-based ligand and a metal, and an ink composition including the metal complex. The bipyridine-based metal complex may be self-dispersed without requiring a dispersing agent and may be used as a colorant per se. Furthermore, the metal complex, when binding with a common colorant, may produce various colors and exhibit enhanced durability including light resistance. In addition, the metal complex includes a hydrophilic group-containing ligand coordinating with the metal, in addition to the bipyridine-based ligand, and thus, has a bulky structure. Therefore, dispersion stability is enhanced by a self-dispersion system based on a steric hindrance due to the bulky structure of the metal complex and an electrostatic repulsive force between the charged metal and the hydrophilic group-containing ligand, thus enhancing a long-term storage stability.

21 Claims, No Drawings

SELF-DISPERSIBLE BIPYRIDINE-BASED METAL COMPLEX AND INK COMPOSITION COMPRISING THE SAME

CROSS-REFERENCE TO RELATED APPLICATIONS

This application claims priority from Korean Patent Application No. 2003-55023, filed on Aug. 8, 2003, in the Korean Intellectual Property Office, the disclosure of which is incorporated herein in its entirety by reference.

BACKGROUND OF THE INVENTION

1. Field of the Invention

The present invention relates to a self-dispersible bipyridine-based metal complex and an ink composition comprising the same. More particularly, the present invention relates to a bipyridine-based metal complex that may be efficiently dispersed even in the absence of a dispersing agent, and an ink composition comprising the same, wherein the ink composition has a desirable coloring property, durability, and dispersion stability.

2. Description of the Related Art

In general, colorants produce their specific colors by selectively absorbing or reflecting visible light, and are classified into dyes and pigments.

Dyes are substances that are used to color subject matters such as fibers, leathers, furs, and papers, and have considerable fastness to daylight washing, friction, and the like. Pigments are particles having color materials and are adhered to the surfaces of subject matters by physical means such as adhesion, instead of directly coloring the surfaces of the subject matters, producing their specific colors.

Dyes are used as colorants for foods, medicines, cosmetics, and ink-jet inks, in addition to the above-described fibers, leathers, furs, and papers. Pigments are used in paints, printing inks, plastic coloration, rubber coloration, furniture making, textile printing, paper making, ceramics, and the like.

Colors produced by these colorants are determined by which wavelength of visible light ranging from 3,000 to 7,000 Å the color material particles reflect or transmit. Based on such characteristics, colorants may be classified into two types, depending on molecular structures: organic colorants and inorganic colorants. Although coloration mechanisms are not clearly elucidated, for organic colorants, coloration is carried out by a cycle of light absorption, transmission, and emission through conjugation of double bonds. For inorganic colorants, when a ligand coordinating with a metal absorbs light, a ligand-metal complex is changed from an excited energy state to a ground energy state, thus emitting light, which produces colors.

Generally, organic colorants have wide coloring ranges and produce bright and clear colors, but have ineffective light resistance, such as decoloration or discoloration. On the other hand, inorganic colorants have excellent durability, including light resistance, but also have problems such as narrow coloring ranges and simple color types.

Hereto, various compound colorants have been known. Pigment metal complexes are disclosed in U.S. Pat. Nos. 3,971,739, 3,987,023, 4,077,953, 4,152,324, and Japanese Patent Laid-Open Publication No. 2001-152044. These patents disclose a method for preparing an azo compound-metal complex by a coordination bond and a covalent bond. According to this method, however, there are restrictions in that a specific functional group of an azo group is required, and coexistence of functional groups for the coordination bond and the covalent bond requires appropriate spacing between the coordination bond and the covalent bond when the functional groups react with the metal. In addition, the above-disclosed complexes have an unsatisfactory durability and coloring property. Thus, there is a need for improvements.

SUMMARY OF THE INVENTION

The present invention provides a bipyridine-based metal complex which may be dispersed in the absence of a dispersing agent, with improvements in coloring property and durability and an ink composition comprising the same which is improved in storage stability and light resistance.

According to an aspect of the present invention, a bipyridine-based metal complex may be represented by the following Formula I:

Formula I

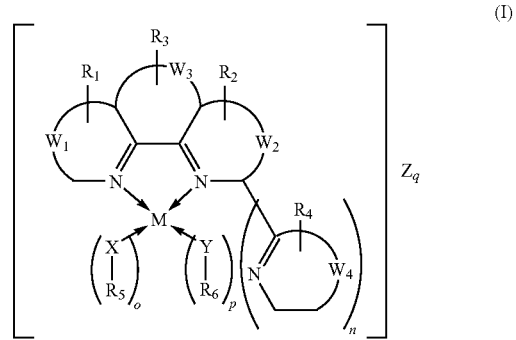

wherein $W_1$, $W_2$, and $W_4$ are each independently atoms required to form a 4- to 8-membered heteroaryl group or heterocycloalkenyl group;

$W_3$ represents atoms required to form one of a 0- to 8-membered cycloalkyl group, a cycloalkenyl group, an aryl group, a heteroaryl group, a heterocycloalkyl group, and a heterocycloalkenyl group;

n is an integer of 0 to 100;

$R_1$, $R_2$, $R_3$, and $R_4$ are mono-substituents or a same or different multi-substituents, and are each independently selected from the group consisting of a hydrogen atom, a halogen atom, a nitro group, $-SO_3H$, $-COOH$, a substituted or unsubstituted alkyl group of $C_1$-$C_{20}$, a substituted or unsubstituted heteroalkyl group of $C_1$-$C_{20}$, a hydroxy group, an amino group, a cyano group, a substituted or unsubstituted alkenyl group of $C_2$-$C_{20}$, a substituted or unsubstituted alkoxy group of $C_1$-$C_{20}$, a substituted or unsubstituted alkylsulfonamide group of $C_1$-$C_{20}$, a substituted or unsubstituted arylsulfonamide group of $C_6$-$C_{20}$, a substituted or unsubstituted acylamino group of $C_1$-$C_{20}$, an alkylureido group of $C_1$-$C_{20}$, an arylureido group of $C_6$-$C_{20}$, an alkoxycarbonyl group of $C_2$-$C_{20}$, an alkoxycarbonylamino group of $C_2$-$C_{20}$, a carbamoyl group, a sulfamoyl group, a sulfo group or its salt, a carboxyl group or its salt, a substituted or unsubstituted hydroxyalkyloxyalkyl group of $C_1$-$C_{20}$, a substituted or unsubstituted dialkylaminoalkyl group of $C_1$-$C_{20}$, a substituted or unsubstituted pyridylalkyl group of $C_6$-$C_{20}$, a substituted or unsubstituted pyridyl group of $C_5$-$C_{20}$, a substituted or unsubstituted imidazolyl group of $C_6$-$C_{20}$, a hydrazine group, a hydrazone group, a substituted or unsubstituted pyridylalkyl group of $C_1$-$C_{20}$, a substituted or unsubstituted aryl group of $C_6$-$C_{20}$, a substituted or unsubstituted arylalkyl group of $C_6$-$C_{20}$, a substituted or unsubstituted heteroaryl group of $C_6$-$C_{20}$, a heteroarylalkyl group of $C_6$-$C_{20}$, a substituted or unsubstituted heteroarylalkenyl group of $C_6$-$C_{20}$, and a substituted or unsubstituted heterocycloalkyl group of $C_3$-$C_{20}$;

$R_5$ and $R_6$ are each independently a hydrophilic mono-substituent or a same or different hydrophilic multi-substituent;

M is a metal atom selected from Groups III through XIV;

X is an anionic moiety;

Y is a neutral moiety;

Z is a counterion;

o, p, and q are each independently an integer of 0 to 10, wherein a sum of o and p is not equal to zero.

According to another aspect of the present invention, a bipyridine-based metal complex may be represented by the following Formula II:

Formula II $$\left[ \begin{array}{c} (A_1)_l \quad (A_3)_k \quad (A_2)_j \\ R_1 \quad (R_3)_l \quad (R_2)_k \\ W_1 \quad W_3 \quad W_2 \\ N \quad N \quad (A_4)_m \\ M \quad (R_4)_m \\ X \quad Y \\ R_7 \quad R_8 \quad N \quad W_4 \\ A_1 \quad A_1 \end{array} \right] Z_q$$

wherein $W_1$, $W_2$, and $W_4$ are each independently atoms required to form a 4- to 8-membered heteroaryl group or heterocycloalkenyl group;

$W_3$ represents atoms required to form one of a 0- to 8-membered cycloalkyl group, a cycloalkenyl group, an aryl group, a heteroaryl group, a heterocycloalkyl group, and a heterocycloalkenyl group;

n is an integer of 0 to 100;

$A_1$, $A_2$, $A_3$, and $A_4$ are each independently a same or different common colorant and respectively bind with the ring compounds, $W_1$, $W_2$, $W_3$, and $W_4$;

i, j, k, and m are each independently 0 or 1, wherein a sum of i, j, k, and m is not equal to zero;

where all of i, j, k, and m are 1, and $R_1$, $R_2$, $R_3$, and $R_4$ are each a linker;

where i is 0, $R_1$ is a mono-substituent or a same or different multi-substituent and is one of a hydrogen atom, a halogen atom, a nitro group, —$SO_3H$, —COOH, a substituted or unsubstituted alkyl group of $C_1$-$C_{20}$, a substituted or unsubstituted heteroalkyl group of $C_1$-$C_{20}$, a hydroxy group, an amino group, a cyano group, a substituted or unsubstituted alkenyl group of $C_2$-$C_{20}$, a substituted or unsubstituted alkoxy group of $C_1$-$C_{20}$, a substituted or unsubstituted alkylsulfonamide group of $C_1$-$C_{20}$, a substituted or unsubstituted arylsulfonamide group of $C_6$-$C_{20}$, a substituted or unsubstituted acylamino group of $C_1$-$C_{20}$, an alkylureido group of $C_1$-$C_{20}$, an arylureido group of $C_6$-$C_{20}$, an alkoxycarbonyl group of $C_2$-$C_{20}$, an alkoxycarbonylamino group of $C_2$-$C_{20}$, a carbamoyl group, a sulfamoyl group, a sulfo group or its salt, a carboxyl group or its salt, a substituted or unsubstituted hydroxyalkyloxyalkyl group of $C_1$-$C_{20}$, a substituted or unsubstituted dialkylaminoalkyl group of $C_1$-$C_{20}$, a substituted or unsubstituted pyridylalkyl group of $C_6$-$C_{20}$, a substituted or unsubstituted pyridyl group of $C_5$-$C_{20}$, a substituted or unsubstituted imidazolyl group of $C_6$-$C_{20}$, a hydrazine group, a hydrazone group, a substituted or unsubstituted pyridylalkyl group of $C_1$-$C_{20}$, a substituted or unsubstituted aryl group of $C_6$-$C_{20}$, a substituted or unsubstituted arylalkyl group of $C_6$-$C_{20}$, a substituted or unsubstituted heteroaryl group of $C_6$-$C_{20}$, a heteroarylalkyl group of $C_6$-$C_{20}$, a substituted or unsubstituted heteroarylalkenyl group of $C_6$-$C_{20}$, and a substituted or unsubstituted heterocycloalkyl group of $C_3$-$C_{20}$;

where j is 0, $R_2$ is referred to in a description of $R_1$ where i is 0;

where k is 0, $R_3$ is referred to in a description of $R_1$ where i is 0;

where m is 0, $R_4$ is referred to in a description of $R_1$ where i is 0;

$R_5$ and $R_6$ are each independently a hydrophilic mono-substituent or a same or different hydrophilic multi-substituent;

M is a metal atom selected from Groups III through XIV;

X is an anionic ligand;

Y is a neutral ligand;

Z is a counterion;

o, p, and q are each independently an integer of 0 to 10, wherein a sum of o and p is not equal to zero.

In Formula I, $R_5$ and $R_6$ may be each independently one or more selected from the group consisting of —OA, —COOA, —$SO_2NH_2$, —$R'SO_2A$, —$PO_3H$, —$PO_3A$, —$SO_2NHCOR$, —$NH_2$, and —$NR_3$, where R is an alkyl group of $C_1$-$C_{20}$, an awl group of $C_6$-$C_{20}$, or a heteroaryl group of $C_2$-$C_{20}$, R' is an alkylene group of $C_1$-$C_{20}$, an arylene group of $C_6$-$C_{20}$, or a heteroarylene group of $C_2$-$C_{20}$, and A is one or more selected from the group consisting of a hydrogen atom, an alkaline metal, an ammonium, a substituted or unsubstituted alkyl group of $C_1$-$C_{12}$, and an awl group of $C_6$-$C_{20}$. In Formula II, $R_7$ and $R_6$ may be each independently one or more selected from the group consisting of —CO—, —$SO_3A$-, and —$SO_2A$- where A is one or more selected from the group consisting of a hydrogen atom, an alkaline metal, an ammonium, a substituted or unsubstituted alkyl group of $C_1$-$C_{12}$ and an aryl group of $C_6$-$C_{20}$.

The linker may be selected from the group consisting of —O—, —C(=O)O—, —NH—, —C(=O)NH—, and —CH=N—.

According to yet another aspect of the present invention, an ink composition comprises the bipyridine-based metal complex and an aqueous liquid medium.

Additional aspects and/or advantages of the invention will be set forth in part in the description which follows and, in part, will be obvious from the description, or may be learned by practice of the invention.

DETAILED DESCRIPTION OF THE PREFERRED EMBODIMENTS

Reference will now be made in detail to the embodiments of the present invention, examples of which are illustrated in the accompanying drawings, wherein like reference numerals refer to the like elements throughout. The embodiments are described below to explain the present invention by referring to the figures.

Hereinafter, the present invention will be described in more detail.

The present invention provides a bipyridine-based metal complex represented by Formula I or II in which a bipyridine derivative and a hydrophilic group-containing compound coordinate with a metal. The bipyridine-based metal complex has an effective coloring property as an organic colorant and an effective durability as an inorganic colorant. Furthermore, dispersion stability in a solution is enhanced by a self-dispersion system based on a steric hindrance due to a bulky structure by a coordination bond of a metal with a hydrophilic group-containing ligand and a bipyridine-based ligand and an electrostatic repulsive force between the charged metal and the hydrophilic group-containing ligand, thus enhancing a long-term storage stability.

In Formula I, $R_5$ and $R_6$ are each independently a hydrophilic mono-substituent or a same or different multi-substituent that imparts a dispersion property to the metal complex and the non-limiting examples of the substituent include —OA, —R'OA, —COOA, —R'COOA, $SO_2NH_2$, —R'$SO_2$A, —$PO_3$H, —$PO_3$A, —$SO_2$NHCOR, —$NH_2$, and —$NR_3$, where R is an alkyl group of $C_1$-$C_{20}$, an awl group of $C_6$-$C_{20}$, or a heteroaryl group of $C_2$-$C_{20}$, R' is an alkylene group of $C_1$-$C_{20}$, an arylene group of $C_6$-$C_{20}$, or a heteroarylene group of $C_2$-$C_{20}$, and A is one or more selected from the group consisting of a hydrogen atom, an alkaline metal, an ammonium, a substituted or unsubstituted alkyl group of $C_1$-$C_{12}$, and an awl group of $C_6$-$C_{20}$. In Formula II, $R_7$ and $R_8$ are each independently a hydrophilic mono-substituent or a same or different multi-substituent that imparts a dispersion property to the metal complex and the non-limiting examples of the substituent include —CO—, —$SO_3$A-, and —$SO_2$A- and A is one or more selected from the group consisting of a hydrogen atom, an alkaline metal, an ammonium, a substituted or unsubstituted alkyl group of $C_1$-$C_{12}$, and an aryl group of $C_6$-$C_{20}$.

In the bipyridine-based metal complex of Formula I, at least one of $R_1$, $R_2$, $R_3$, and $R_4$ may have a substituent that reacts with a common colorant. Examples of the substituent include, but are not limited to, —OH, —$NH_2$, —COOH, —$SO_3$H, —$NO_2$, —F, —Cl, —Br, and —I. These functional groups react with —COOH, —OH, —CO, —COH, and —$NH_2$, that are generally included in most common colorants to form a composite colorant.

In Formulas I and II, n is a number of a pyridine moiety bound to a bipyridine-based compound backbone and an integer from 0 to 100, preferably 0 to 10.

In Formulas I and II, M is a coordinating metal and may have a positive charge of +1 to +5. X is an anionic moiety and may have a negative charge of −1 to −6. Z is a counterion and may have a charge of −2 to +2.

M is a metal selected from Groups III through XIV and may be silver (Ag), aluminum (Al), gold (Au), cerium (Ce), cobalt (Co), chromium (Cr), copper (Cu), europium (Eu), iron (Fe), germanium (Ge), indium (In), lanthanum (La), manganese (Mn), nickel (Ni), palladium (Pd), platinum (Pt), rhodium (Rd), ruthenium (Ru), scandium (Sc), silicon (Si), samarium (Sm), titanium (Ti), uranium (U), zinc (Zn), or zirconium (Zr).

As used herein, the term "anionic moiety" refers to a moiety having an anionic property before binding it with the metal M and the term "neutral moiety" refers to a moiety having a neutral property before binding it to the metal M.

X is an anionic moiety having a negative charge of −1 to −6 and may be one or more selected from the group consisting of a halogen atom ion (F−, Cl−, Br−, I−), —R"C(=O)—O*, —R"CN*, —R"OO*, —R"O*, —R"SCN*, —R"$N_3$*, —R"$CO_3$*, and —R"$SO_4$* wherein the * represents the position at which the anionic moiety X binds to the metal M and R" is alkylene of $C_2$-$C_{20}$, arylene of $C_6$-$C_{20}$, heteroarylene of $C_2$-$C_{20}$, or —($CH_2CH_2O$)$_z$— where Z is 1 to 50.

Y is a neutral moiety and may be a monodentate ligand, a bidentate ligand, or a tridentate ligand. Y may be one or more selected from the group consisting of triphenylphosphinyl, —R"—$NH_2$* where R" is alkylene of $C_2$-$C_{20}$, arylene of $C_6$-$C_{20}$, heteroarylene of $C_2$-$C_{20}$, or —($CH_2CH_2O$)$_z$— where Z is 1 to 50, 2,2'-bipyridyl, 1,10-phenanthrolyl, 2,2',2"-terpyridyl, and ligands represented by the following structural Formulas:

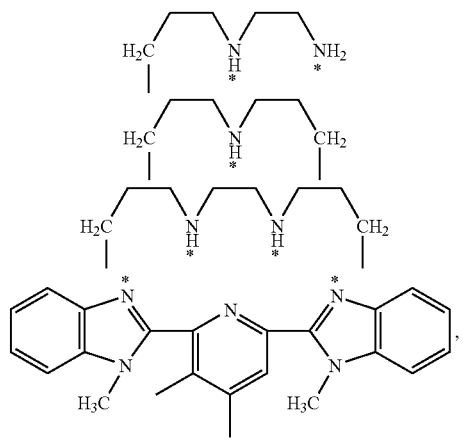

wherein the * represents the position at which the moiety Y binds to the metal M.

Z is a counterion and may be a cation or an anion having a charge of −2 to 2 to neutralize the metal complex. The anion for Z may be selected from the group consisting of a halide ion (F—, Cl—, Br—, or I—, for example), a sulfite ion, an alkylsulfite ion of $C_1$-$C_{10}$, a sulfate ion, an alkylsulfate ion of $C_1$-$C_{10}$, a nitrate ion, a nitrite ion, a perchloric acid ion, a carboxylate ion of $C_1$-$C_{10}$ (acetate, trifluoroacetate, or stearylate, for example), a salicylate ion, a benzoate ion, a hexafluorophosphate ion, and a tetrafluoroborate ion. The cation for Z may be a (monovalent) lithium, a (monovalent) sodium, a (monovalent) potassium, a (monovalent) ammonium, or a (monovalent) phosphonium.

In preparation of the bipyridine-based metal complex represented by Formula I or II, non-limiting examples of a metal M ion donor include zinc chloride, zinc sulfate, zinc nitrate, zinc acetate, nickel chlorides), nickel sulfate (II), nickel nitrate (II), nickel acetate (II), nickel stearate (II), bis(2,4-pentanedionato)diaquanickel (II), bis(dimethylglyoxymato) nickel (II), bis(3-methoxycarbonyl-2,4-tetodecanedionato) nickel (II), tris(glycineamido) nickel (II), tetraphenyl borate, cobalt hexaneammine(III) chlorinated product, tris(ethylenediamine) cobalt(III) chlorinated product, cis-dichlorotetraamine cobalt(III) chlorinated product, ammonium tetranitrodiamine cobalt(III) acid, potassium hexacyano cobalt(III) acid, copper chlorides(II), copper tetrafluoro borate(II), bis (ethylenediamine) copper(II) sulfate, rhodium chloride(II), rhodium sulfate(II), dirhodium tetraacetic acid(II), hexaammine rhodium(III) chloride, potassium hexacyanorhodium (III), rutheniumbromide(III), hexaammine ruthenium(III) bromide, potassium hexacyano ruthenium(II) acid, palladium sulfate(II), ammonium acid of tetrachloro palladium(II), tetraammine palladium(II) chloride, bisethylendiamine platinum(II) chloride, hexaammine platinum(IV) chloride, and tris(ethylenediamine) platinum(IV) chloride.

An illustrative example of a ligand backbone of Formula I is represented in Formula III below in which n of Formula I is 0 and the $W_3$ ring is absent. The compound of Formula III has a 2,2'-bipyridine derivative backbone as a ligand that may coordinate with the metal M to form a metal complex, and may be used as a colorant that produces a specific color:

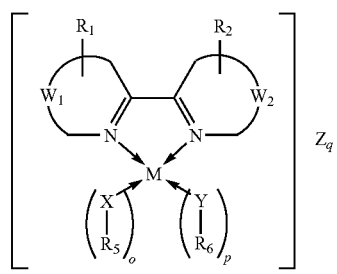

Formula III wherein $W_1$, $W_2$, M, Z, X, Y, o, p, q, $R_1$, $R_2$, $R_5$, and $R_6$ are referred to above.

To use a metal complex obtained by a coordination bond between the 2,2'-bipyridine derivative ligand and the metal M as a colorant, the metal complex does not necessarily have the above-illustrated examples of the substituents, $R_1$ and $R_2$. A 2,2'-bipyridine-containing compound may also be used for coordination with the metal M.

An illustrative example of a ligand backbone of Formula I is represented in Formula IV below. The compound of Formula IV has a 1,10-phenanthroline derivative backbone as a ligand that may coordinate with the metal M to form a metal complex and may be used as a colorant that produces a specific color:

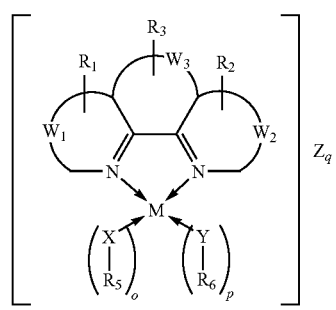

Formula IV wherein $W_1$, $W_2$, $W_3$, M, Z, X, Y, o, p, q, $R_1$, $R_2$, $R_3$, $R_5$, and $R_6$ are referred to above.

An illustrative example of a ligand backbone of Formula I is represented in Formula V below. The compound of Formula V has a 2,2':6',2''-terpyridine derivative backbone as a ligand that may coordinate with the metal M to form a metal complex, and may be used as a colorant:

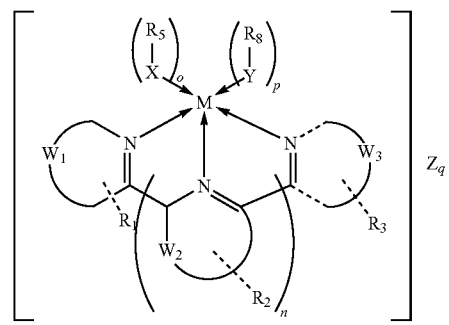

Formula V wherein W1, W2, W3, M, Z, X, Y, o, p, q, R1, R2, R3, R5, and R6 are referred to above.

Examples of the bipyridine-based metal complex of Formula I according to embodiments of the present invention include compounds represented by Formulas VI, VII, VIII, IX, X, XI, and XII below:

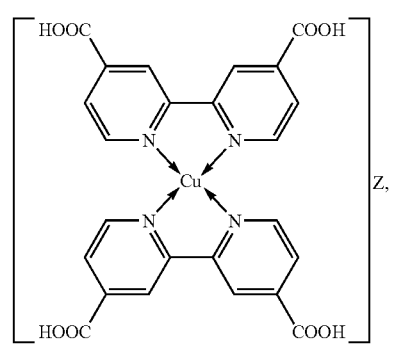

Formula VI wherein Z is $(CH_3COO)_2$, $(SO_4)_2$, $(NO_3)_2$, $(CO_3)_2$, $(ClO_4)_2$, or $Cl_2$;

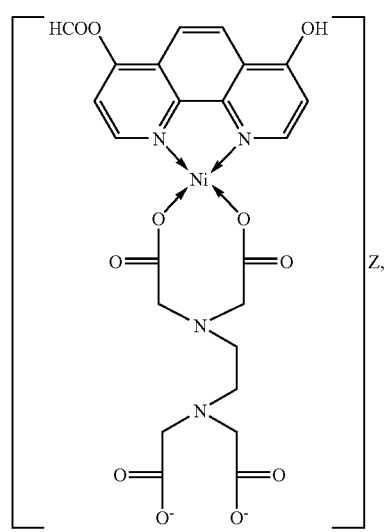

Formula VII wherein Z is 2Na⁺ or 2K⁺;

Formula VIII

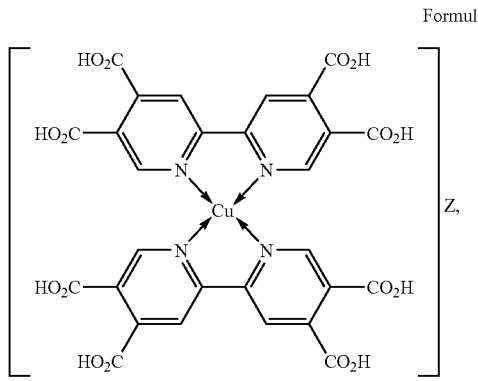

wherein Z is (CH₃COO)₂, (SO₄)₂, (NO₃)₂, (CO₃)₂, (ClO₄)₂, or Cl₂;

Formula IX

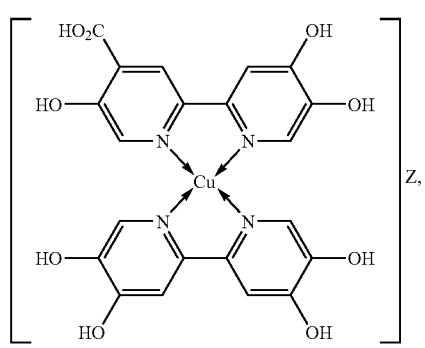

wherein Z is (CH₃COO)₂, (SO₄)₂, (NO₃)₂, (CO₃)₂, (ClO₄)₂, or Cl₂;

Formula X

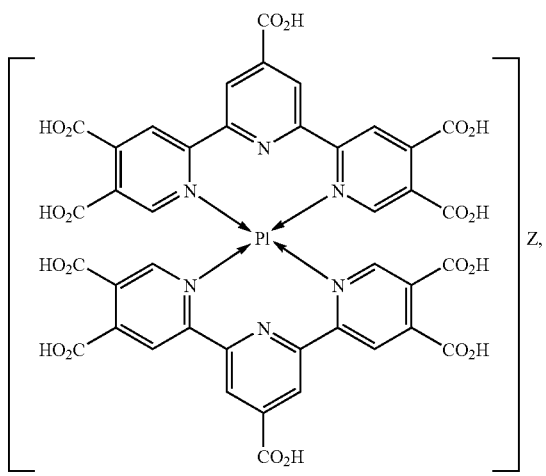

wherein Z is (CH₃COO)₂, (SO₄)₂, (NO₃)₂, (CO₃)₂, (ClO₄)₂, or Cl₂;

Formula XI

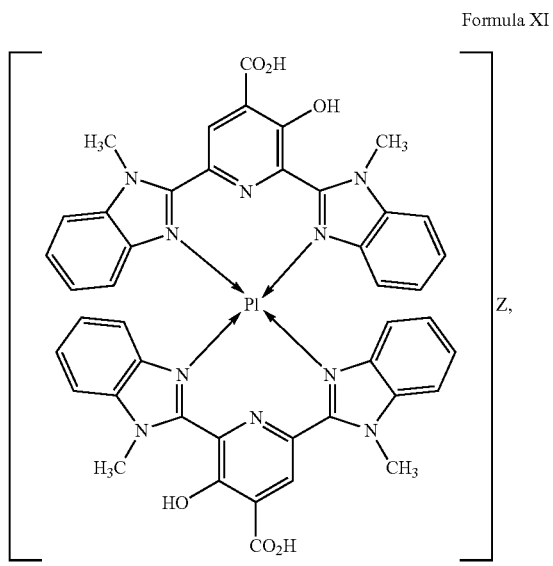

wherein Z is (CH₃COO)₂, (SO₄)₂, (NO₃)₂, (CO₃)₂, (ClO₄)₂, or Cl₂; and

Formula XII

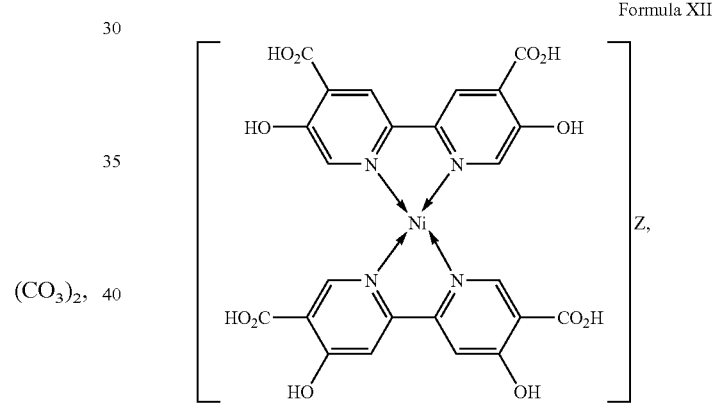

wherein Z is (CH₃COO)₂, (SO₄)₂, (NO₃)₂, (CO₃)₂, (ClO₄)₂, or Cl₂.

Meanwhile, in the bipyridine-based metal complex of Formula II, the A is a common colorant and may be an organic colorant or an inorganic colorant. The A may be a dye or a pigment that may react with a bipyridine-based ligand and includes the following non-limiting examples.

Examples of the dye include C.I. DIRECT BLACK 9, 17, 19, 22, 32, 56, 91, 94, 97, 166, 168,174, and 199; C.I. DIRECT BLUE 1, 10, 15, 22, 77, 78, 80, 200, 201, 202, 203, 207, and 211; C.I. DIRECT RED 2, 4, 9, 23, 31, 39, 63, 72, 83, 84, 89, 111, 173, 184, and 240; and C.I. DIRECT YELLOW 8, 9, 11, 12, 27, 28, 29, 33, 35, 39, 41, 44, 50, 53, and 58.

Examples of the pigment include a carbon black, graphite, a vitreous carbon, an activated charcoal, an activated carbon, anthraquinone, a phthalocyanine blue, a phthalocyanine green, diazos, monoazos, pyranthrones, perylene, quinacridone, and indigoid pigments.

A novel colorant obtained by binding between a bypridine-based ligand-metal complex and the above common colorant may generally be used in fibers, leathers, furs, papers, foods, medicines, cosmetics, inkjet inks, printing inks, paints, plastic coloration, rubber coloration, furniture making, textile printing, paper making, and ceramics.

In formulas of the present invention, a carbon number of a heteroaryl group is 2 to 20, and a carbon number of a heterocycloalkenyl group is 2 to 20.

Examples of the unsubstituted alkyl group of $C_1$-$C_{20}$ in Formulas I and II include methyl, ethyl, propyl, isobutyl, sec-butyl, pentyl, iso-amyl, and hexyl. One or more hydrogen atoms on the alkyl group may be substituted by a halogen atom, a hydroxy group, a nitro group, a cyano group, an amino group, an amidino group, hydrazine, hydrazone, a carboxyl group or its salt, a sulfonyl group or its salt, a phosphonyl group or its salt, an alkyl group of $C_1$-$C_{20}$, an alkenyl group of $C_2$-$C_{20}$, an alkynyl group of $C_2$-$C_{20}$, a heteroalkyl group of $C_1$-$C_{20}$, an aryl group of $C_6$-$C_{20}$, an arylalkyl group of $C_6$-$C_{20}$, a heteroaryl group of $C_6$-$C_{20}$, or a heteroarylalkyl group of $C_6$-$C_{20}$.

The unsubstituted alkenyl group of $C_2$-$C_{20}$ as used herein refers to an alkyl group that includes a carbon-carbon double bond in a central portion or an end of the alkyl as referred to above. Examples of the alkenyl group include ethylene, propylene, butylene, and hexylene. One or more hydrogen atoms on the alkenyl group may be substituted by the same substituents as those referred to above in the alkyl group.

The heteroalkyl group as used herein refers to an alkyl group containing nitrogen, sulfur, oxygen, or phosphorus in the alkyl as referred to above. Examples of the heteroalkyl group include methoxy, ethoxy, propoxy, butoxy, and t-butoxy. The heteroalkyl group with a substituent may be a haloalkoxy radical, such as fluoromethoxy, chloromethoxy, trifluoromethoxy, trifluoroethoxy, fluoroethoxy, and fluoropropoxy. One or more hydrogen atoms on the heteroalkyl group may be substituted by the same substituents referred to above in the alkyl group.

The aryl group as used herein, which is used alone or in combination, refers to a carbocyclic aromatic system of 6-20 carbon atoms having one or more rings. The rings may be attached to each other as a pendant group or may be fused. The term, "aryl" refers to an aromatic radical such as phenyl, naphthyl, and tetrahydronaphthyl. The aryl group may have a substituent such as haloalkylene, nitro, cyano, alkoxy, and lower alkylamino. One or more hydrogen atoms on the aryl group may be substituted by the same substituents referred to in the alkyl group.

The arylalkyl group as used herein refers to a lower alkyl, for example, methyl, ethyl, or propyl appended to the aryl referred to above. Examples of the arylalkyl group include benzyl and phenylethyl. One or more hydrogen atoms on the arylalkyl group may be substituted by the same substituents referred to above in the alkyl group.

The heteroaryl group as used herein refers to a monovalent monocyclic or bicyclic aromatic compound of 6-20 carbon atoms containing one, two or three hetero atoms selected from N, O, P or S. One or more hydrogen atoms on the heteroaryl group may be substituted by the same substituents referred to above in the alkyl group.

The heteroarylalkyl group as used herein refers to an alkyl group appended to the heteroaryl referred to above. One or more hydrogen atoms on the heteroarylalkyl group may be substituted by the same substituents referred to above in the alkyl group.

An ink composition including the bipyridine-based metal complex of Formula I or II will now be described in detail.

The ink composition of the present invention includes an aqueous liquid medium and a colorant. Here, as the colorant, the bipyridine-based metal complex of Formula I or II alone or a combination of the bipyridine-based metal complex and a common colorant such as a dye and pigment may be used. The bipyridine-based metal complex of the Formula I or II may be used in an amount of 0.1 to 10 parts by weight, based on 100 parts by weight of the aqueous liquid medium. If the content of the bipyridine-based metal complex of the Formula I or II exceeds 10 parts by weight, a storage stability may be lowered. On the other hand, if the content of the bipyridine-based metal complex of the Formula I or II is less than 0.1 parts by weight, durability may be lowered. When the ink composition includes a combination of the bipyridine-based metal complex of the Formula I or II and a common colorant, the common colorant may be used in an amount of 1 to 10,000 parts by weight, based on 100 parts by weight of the bipyridine-based metal complex of the Formula I or II.

The aqueous liquid medium may be water alone, or a mixture of water with at least one organic solvent. Preferably, the aqueous liquid medium is used in an amount of 0.5 to 50 parts by weight, based on 100 parts by weight of the solid of the ink composition. Here, the solid of the ink composition refers to the content of the colorant in the absence of an additive and the total content of the colorant and the additive in the presence of the additive. The aqueous liquid medium containing the organic solvent enables an optimal adjustment of the viscosity and surface tension of the ink composition.

The organic solvent is not particularly limited and may be a hydrocarbon solvent selected from the group consisting of alcohols such as methylalcohol, ethylalcohol, n-propylalcohol, isopropylalcohol, n-butylalcohol, sec-butylalcohol, t-butylalcohol, and isobutylalcohol; ketones such as acetone, methylethylketone, and diacetone alcohol; esters such as ethyl acetate and ethyl lactate; polyhydric alcohols such as ethyleneglycol, diethyleneglycol, triethyleneglycol, propyleneglycol, butyleneglycol, 1,4-butanediol, 1,2,4-butanetriol, 1,5-pentanediol, 1,2-hexanediol, 1,6-hexanediol, 1,2,6-hexanetriol, hexyleneglycol, glycerol, glycerol ethoxylate, and trimethylolpropane ethoxylate; lower alkyl ethers such as ethyleneglycol monomethyl ether, ethyleneglycol monoethyl ether, diethyleneglycol methyl ether, diethyleneglycol ethyl ether, triethyleneglycol monomethyl ether, and triethyleneglycol monoethyl ether; nitrogen-containing compounds such as 2-pyrrolidone, N-methyl-2-pyrrolidone, and caprolactam; dimethyl sulfoxide, tetramethylenesulfone, and thioglycol.

The ink composition of the present invention may further include an additive such as a viscosity modifier, a surfactant, a metal oxide, a wetting agent, and a storage stabilizer. The additive may be used in an amount of 0.5 to 30 parts by weight, based on 100 parts by weight of the colorant.

The surfactant serves to stabilize the jetting performance of ink from a nozzle by adjusting the surface tension of the ink composition. An anionic or non-ionic surfactant may be used.

The viscosity modifier serves to adjust the viscosity of the ink composition to maintain a smooth jetting of ink and may be one selected from polyvinylalcohol, casein, and carboxymethylcellulose.

The ink composition of the present invention may further include an acid or a base. The acid or base is used to increase solubility of the wetting agent in a solvent and to stabilize a pigment.

The ink composition of the present invention may be prepared using the components referred to above in the following procedure.

First, the bipyridine-based metal complex of the Formula I or II is added to the aqueous liquid medium. Then, an additive such as a common colorant, a viscosity adjustor, and a surfactant is selectively added to the reaction mixture and thoroughly stirred in a stirrer to obtain a uniform solution. The uniform solution is filtered through a filter to obtain the ink composition of an embodiment of the present invention.

Meanwhile, there are no particular limitations on the usage of the bipyridine-based metal complex of the Formula I or II according to embodiments of the present invention. Therefore, the bipyridine-based metal complex of the Formula I or II may be used in a toner composition, various paints, or a coating solution, in addition to the ink composition.

Hereinafter, the present invention will be described with reference to the following Examples but is not limited thereto. In the following Examples, property evaluations were done for ink compositions. However, it is understood that the property evaluations may be applied to wet toners, dry toners, paints, and coating solutions.

Synthesis Example 1

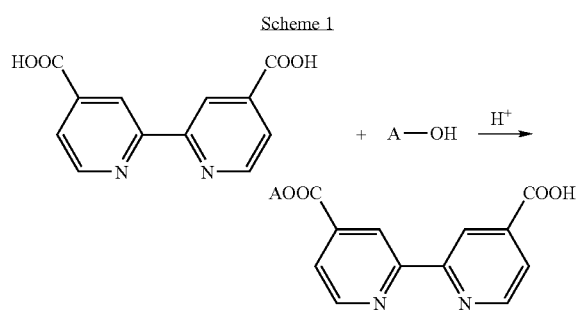

Scheme 1

(1) 10.2 g of 2,2'-bipyridine-4,4'-dicarboxylic acid was reacted with 11.6 g of 2-amino-5-naphtol-7-sulfonic acid (A-OH) as a dye in a 250 ml rounded bottom flask containing 100 ml of toluene in the presence of 0.5 g of p-toluene sulfonic acid as an acid catalyst by reduced-pressure distillation for 6 hours. At this time, water was continuously removed using a Dean-Stark apparatus.

The reaction was terminated by addition of an aqueous 0.1 N NaOH solution. An organic layer was extracted by cyclohexane and an aqueous saturated NaCl solution and concentrated to give 16.5 g of a product of Scheme 1.

Synthesis Example 2

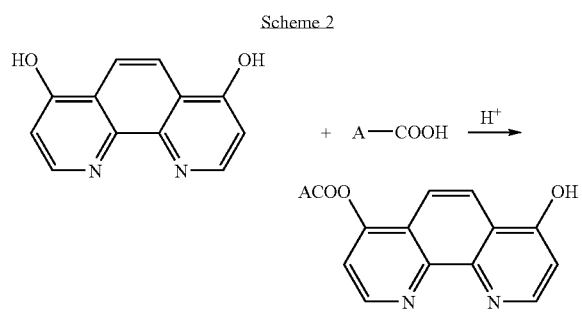

Scheme 2

14.8 g of 4,7-dihydroxy-1,10-phenanthroline as a starting material of Scheme 1 was reacted with 12.3 g of a carbon black (A—COOH) in 100 ml of xylene in the presence of 0.4 g of sulfuric acid as an acid catalyst by a reduced-pressure distillation. The reaction was terminated by addition of an aqueous 0.1 N KOH solution and hot-filtered through a membrane filter placed in a funnel to give 19.5 g of an ester product of Scheme 2.

Synthesis Example 3

12.3 g of the product of Synthesis Example 1 was dissolved in 100 ml of water, and 8.5 g of cupric acetate was added thereto. The reaction mixture was distilled under a reduced pressure for 12 hours. An organic layer was extracted with cyclohexane and an aqueous saturated NaCl solution and concentrated to give 18.5 g of a bipyridine-based metal complex represented by Formula VI.

Synthesis Example 4

19.5 g of the product of Synthesis Example 2 was dissolved in 100 ml of water and 10.3 g of nickel nitrate(II) was added thereto. The reaction mixture was distilled under a reduced pressure for 10 hours. An organic layer was extracted with toluene and an aqueous saturated NaCl solution and concentrated to give 24.3 g of a bipyridine-based metal complex represented by Formula VII.

Example 1

4.0 g of the bipyridine-based metal complex of Formula VII, 77.0 g of water, 3.0 g of diethylene glycol, 8.0 g of ethylene glycol, and 8.0 g of glycerine were mixed and thoroughly stirred in a stirrer for 30 minutes or more to obtain a uniform solution. Then, the uniform solution was filtered through a filter with a pore size of 0.45 μm to yield an ink composition.

Examples 2-6

Ink compositions were prepared in the same manner as in Example 1, except that the compounds of Formulas VIII, IX, X, XI, and XII were used instead of the metal complex of Formula VII.

Comparative Example 1

An ink composition was prepared in the same manner as in Example 1, except that a carbon black (RAVEN 5250, COLUMBIAN CO.) was used instead of the complex compound of Formula VII.

Comparative Example 2

An ink composition was prepared in the same manner as in Example 1, except that a carbon black (REGAL 330, CABOT CO.) was used instead of the metal complex of Formula Comparative Example 3

An ink composition was prepared in the same manner as in Example 1, except that a carbon black (BLACK PEARL L, CABOT CO.) was used instead of the metal complex of Formula VII.

Comparative Example 4

An ink composition was prepared in the same manner as in Example 1, except that a carbon black (NO. 25B, MITSUBISHI CO.) was used instead of the metal complex of Formula VII.

Comparative Example 5

An ink composition was prepared in the same manner as in Example 1, except that a carbon black (NO. 258, MITSUBISHI CO.) was used instead of the metal complex of Formula VII.

Comparative Example 6

An ink composition was prepared in the same manner as in Example 1, except that a carbon black (VALCAN XC-72R, CABOT CO.) was used instead of the metal complex of Formula VII.

Properties of ink compositions of Examples 1-6 and Comparative Examples 1-6 were evaluated according to the following methods.

(1) Long-Term Storage Stability 100 ml of each ink composition of Examples 1-6 and Comparative Examples 1-6 was placed in a thermostable glass bottle, sealed, and deposited in a 60° C. thermostatic bath. After two months, the presence of a precipitate was observed.

According to the evaluation results, no precipitates were observed in the ink compositions of Examples 1-6. It may be seen from the results that the ink compositions of Examples 1-6 containing the metal complex colorants of the present invention exhibit effective storage stability, similar to the ink compositions of Comparative Examples 1-6.

(2) Dispersion Stability

The ink compositions of Examples 1-6 and Comparative Examples 1-6 were subjected to a thermal cycle (TC) of 60° C. for 4 hours and −40° C. for 4 hours 10 times, and then filtered through a 1 μm membrane. The dispersion stability was evaluated by measuring a time required for the filtration, and the results are presented in Table 1 below.

$A=\{$Filtration duration after $TC$−Filtration duration before $TC\}$/Filtration duration before $TC \times 100$ (%)

○: A<10
Δ: 10≦A<20
X: A>20

TABLE 1

| Section | Examples | | | | | | Comparative Examples | | | | | |
|---|---|---|---|---|---|---|---|---|---|---|---|---|
|  | 1 | 2 | 3 | 4 | 5 | 6 | 1 | 2 | 3 | 4 | 5 | 6 |
| Evaluation | ○ | ○ | ○ | ○ | ○ | ○ | ○ | Δ | X | ○ | Δ | Δ |

As shown in Table 1, the ink compositions of Examples 1-6 using the metal complex colorants of the present invention exhibited effective dispersion stability, compared to the ink compositions of Comparative Examples 1-6.

(3) Nozzle Clogging

The ink compositions of Examples 1-6 and Comparative Examples 1-6 were kept in SAMSUNG ELECTRONICS CO., LTD. ink cartridges at room temperature (25° C.) and low temperature (−18° C.) each for 2 weeks, and then printing was carried out. The degree of nozzle clogging that prevents ink ejection was evaluated according to the following criteria, and the results are presented in Table 2 below.

○: No nozzles were clogged
Δ: One to two nozzles were clogged
X: Three or more nozzles were clogged

TABLE 2

| Section | Examples | | | | | | Comparative Examples | | | | | |
|---|---|---|---|---|---|---|---|---|---|---|---|---|
|  | 1 | 2 | 3 | 4 | 5 | 6 | 1 | 2 | 3 | 4 | 5 | 6 |
| 25° C. | ○ | ○ | ○ | ○ | ○ | ○ | Δ | X | ○ | Δ | ○ | ○ |
| −18° C. | ○ | ○ | ○ | ○ | ○ | ○ | X | X | ○ | X | ○ | ○ |

(4) Light Resistance

Each ink composition of Examples 1-6 and Comparative Examples 1-6 was placed in a SAMSUNG ELECTRONICS CO., LTD. ink cartridge and a solid pattern of 2 cm×2 cm was printed. The solid pattern was exposed to light in a Q-SUN Xenon Test Chamber for 100 hours. OD values before and after the test were measured and evaluated according to the following criteria. The results are presented in Table 3 below.

$A=OD$ after test/$OD$ before test×100(%)

○: A≧90
Δ: 75≦A<90
X: A<75

TABLE 3

| Section | Examples | | | | | | Comparative Examples | | | | | |
|---|---|---|---|---|---|---|---|---|---|---|---|---|
|  | 1 | 2 | 3 | 4 | 5 | 6 | 1 | 2 | 3 | 4 | 5 | 6 |
| Evaluation | ○ | ○ | ○ | ○ | ○ | ○ | ○ | Δ | ○ | X | Δ | Δ |

As shown in Table 3, the ink compositions of Examples 1-6 exhibited effective light resistance. On the other hand, the ink compositions of Comparative Examples 4-6 exhibited ineffective light resistance.

A self-dispersible bipyridine-based ligand-metal complex according to an embodiment of the present invention may be used as a colorant per se. Furthermore, the metal complex, when binding with a common colorant, may produce various colors and exhibit enhanced durability such as light resistance. In addition, the metal complex includes a hydrophilic group-containing ligand coordinating with the metal, in addition to the bipyridine-based ligand, and thus, has a bulky structure. Therefore, dispersion stability is enhanced by a self-dispersion system based on a steric hindrance due to the bulky structure of the metal complex and an electrostatic repulsive force between the charged metal and the hydrophilic group-containing ligand, thus enhancing a long-term storage stability. Therefore, the self-dispersible bipyridine-based ligand-metal complex may generally be used as a colorant for fibers, leathers, furs, papers, foods, medicines, cosmetics, paints, printing ink, inkjet inks, plastic coloration, rubber coloration, furniture making, textile printing, paper making, and ceramics.

The present invention may be embodied as a bipyridine-based metal complex represented by the following Formula I:

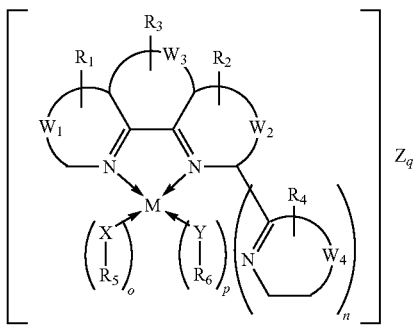

(I)

wherein $W_1$, $W_2$, and $W_4$ are each independently atoms required to form a 4- to 8-membered heteroaryl group or heterocycloalkenyl group;

$W_3$ refers to atoms required to form one of a 0- to 8-membered cycloalkyl group, a cycloalkenyl group, an aryl group, a heteroaryl group, a heterocycloalkyl group, and a heterocycloalkenyl group;

n is an integer of 0 to 100;

$R_1$, $R_2$, $R_3$, and $R_4$ are mono-substituents or a same or different multi-substituents, and are each independently one of a hydrogen atom, a halogen atom, a nitro group, —$SO_3H$, —COOH, a substituted or unsubstituted alkyl group of $C_1$-$C_{20}$, a substituted or unsubstituted heteroalkyl group of $C_1$-$C_{20}$, a hydroxy group, an amino group, a cyano group, a substituted or unsubstituted alkenyl group of $C_2$-$C_{20}$, a substituted or unsubstituted alkoxy group of $C_1$-$C_{20}$, a substituted or unsubstituted alkylsulfonamide group of $C_1$-$C_{20}$, a substituted or unsubstituted arylsulfonamide group of $C_6$-$C_{20}$, a substituted or unsubstituted acylamino group of $C_1$-$C_{20}$, an alkylureido group of $C_1$-$C_{20}$, an arylureido group of $C_6$-$C_{20}$, an alkoxycarbonyl group of $C_2$-$C_{20}$, an alkoxycarbonylamino group of $C_2$-$C_{20}$, a carbamoyl group, a sulfamoyl group, a sulfo group or its salt, a carboxyl group or its salt, a substituted or unsubstituted hydroxyalkyloxyalkyl group of $C_1$-$C_{20}$, a substituted or unsubstituted dialkylaminoalkyl group of $C_1$-$C_{20}$, a substituted or unsubstituted pyridylalkyl group of $C_6$-$C_{20}$, a substituted or unsubstituted pyridyl group of $C_5$-$C_{20}$, a substituted or unsubstituted imidazolyl group of $C_6$-$C_{20}$, a hydrazine group, a hydrazone group, a substituted or unsubstituted pyridylalkyl group of $C_1$-$C_{20}$, a substituted or unsubstituted aryl group of $C_6$-$C_{20}$, a substituted or unsubstituted arylalkyl group of $C_6$-$C_{20}$, a substituted or unsubstituted heteroaryl group of $C_6$-$C_{20}$, a heteroarylalkyl group of $C_6$-$C_{20}$, a substituted or unsubstituted heteroarylalkenyl group of $C_6$-$C_{20}$, and a substituted or unsubstituted heterocycloalkyl group of $C_3$-$C_{20}$;

$R_5$ and $R_6$ are each independently a hydrophilic mono-substituent or a same or different hydrophilic multi-substituent;

M is a metal atom selected from Groups III through XIV other than ruthenium (Ru) or copper (I);

X is an anionic moiety;

Y is a neutral moiety;

Z is a counterion;

o, p, and q are each independently an integer of 0 to 10, wherein a sum of o and p is not equal to zero;

wherein X has a negative charge of −1 to −6 and is one or more selected from the group consisting of —R"C(=O)—O*, —R"CN*, —R"OO*, —R"O*, —R"SCN*, —R"$N_3$*, R"$CO_3$*, and R"$SO_4$*, wherein the * represents the position at which the moiety X binds to the metal M and R" is one of an alkylene of $C_2$-$C_{20}$, an arylene of $C_6$-$C_{20}$, heteroarylene of $C_2$-$C_{20}$, and —($CH_2CH_2O$)$_z$— where Z is 1 to 50. n may also be an integer from 0 to 10.

The present invention may also be embodied as a bipyridine-based metal complex represented by the following Formula II:

Formula II

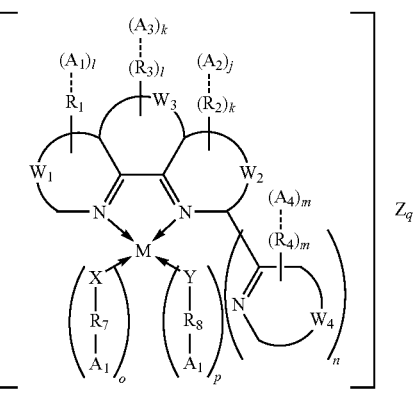

(II)

wherein $W_1$, $W_2$, and $W_4$ are each independently atoms required to form a 4- to 8-membered heteroaryl group or heterocycloalkenyl group;

$W_3$ refers to atoms required to form one of a 0- to 8-membered cycloalkyl group, a cycloalkenyl group, an aryl group, a heteroaryl group, a heterocycloalkyl group, and a heterocycloalkenyl group;

n is an integer of 0 to 100;

$A_1$, $A_2$, $A_3$, and $A_4$ are each independently a same or different colorant and respectively bind with the ring compounds, $W_1$, $W_2$, $W_3$, and $W_4$;

i, j, k, and m are each independently 0 or 1, wherein a sum of i, j, k, and m is not equal to zero;

where all of i, j, k, and m are 1, $R_1$, $R_2$, $R_3$, and $R_4$ are each a linker;

where i is 0, $R_1$ is a mono-substituent or a same or different multi-substituent and is one of: a hydrogen atom, a halogen atom, a nitro group, —$SO_3H$, —COOH, a substituted or unsubstituted alkyl group of $C_1$-$C_{20}$, a substituted or unsubstituted heteroalkyl group of $C_1$-$C_{20}$, a hydroxy group, an amino group, a cyano group, a substituted or unsubstituted alkenyl group of $C_2$-$C_{20}$, a substituted or unsubstituted alkoxy group of $C_1$-$C_{20}$, a substituted or unsubstituted alkylsulfonamide group of $C_1$-$C_{20}$, a substituted or unsubstituted arylsulfonamide group of $C_6$-$C_{20}$, a substituted or unsubstituted acylamino group of $C_1$-$C_{20}$, an alkylureido group of $C_1$-$C_{20}$, an arylureido group of $C_6$-$C_{20}$, an alkoxycarbonyl group of $C_2$-$C_{20}$, an alkoxycarbonylamino group of $C_2$-$C_{20}$, a carbamoyl group, a sulfamoyl group, a sulfo group or its salt, a carboxyl group or its salt, a substituted or unsubstituted hydroxyalkyloxyalkyl group of $C_1$-$C_{20}$, a substituted or unsubstituted dialkylaminoalkyl group of $C_1$-$C_{20}$, a substituted or unsubstituted pyridylalkyl group of $C_6$-$C_{20}$, a substituted or unsubstituted pyridyl group of $C_5$-$C_{20}$, a substituted or unsubstituted imidazolyl group of $C_6$-$C_{20}$, a hydrazine group, a hydrazone group, a substituted or unsubstituted pyridylalkyl group of $C_1$-$C_{20}$, a substituted or unsubstituted aryl group of $C_6$-$C_{20}$, a substituted or unsubstituted arylalkyl group of $C_6$-$C_{20}$, a substituted or unsubstituted heteroaryl group of $C_6$-$C_{20}$, a heteroarylalkyl group of $C_6$-$C_{20}$, a substituted or unsubstituted heteroarylalkenyl group of $C_6$-$C_{20}$, and a substituted or unsubstituted heterocycloalkyl group of $C_3$-$C_{20}$;

where j is 0, $R_2$ is referred to in a description of $R_1$, where i is 0;

where k is 0, $R_3$ is referred to in a description of $R_1$ where i is 0;

where m is 0, $R_4$ is referred to in a description of $R_1$ where i is 0;

$R_7$ and $R_8$ are each independently a hydrophilic mono-substituent or a same or different hydrophilic multi-substituent;

M is a metal atom selected from Groups III through XIV;

X is an anionic ligand;

Y is a neutral ligand;

Z is a counterion;

o, p, and q are each independently an integer of 0 to 10, wherein a sum of o and p is not equal to zero. The linker may be selected from the group consisting of —O—, —C(O)O—, —NH—, —C(=O)NH—, and —CH=N—. n may also be an integer from 0 to 10.

Although a few embodiments of the present invention have been shown and described it would be appreciated by those skilled in the art that changes may be made in these embodiments without departing from the principles and spirit of the invention, the scope of which is defined in the claims and their equivalents.

What is claimed is:

1. A bipyridine-based metal complex represented by the following Formula I:

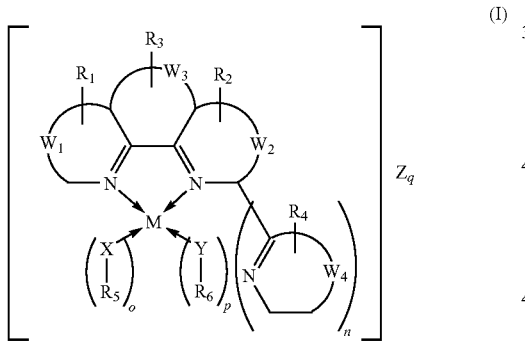

wherein $W_1$ and $W_2$ are each independently atoms required to form a 4- to 8-membered heteroaryl group or heterocycloalkenyl group, and $W_4$ is atoms required to form 4- to 8-membered heteroaryl groups or heterocycloalkenyl groups;

$W_3$ refers to atoms required to form one of a 0- or 6-membered cycloalkyl group, a cycloalkenyl group, an aryl group, a heteroaryl group, a heterocycloalkyl group, and a heterocycloalkenyl group;

n is an integer of 1 to 5;

$R_1$, $R_2$, $R_3$, and $R_4$ are mono-substituents or a same or different multi-substituents, and are each independently one of a hydrogen atom, a halogen atom, a nitro group, —SO₃H, —COOH, a substituted or unsubstituted alkyl group of $C_1$-$C_{20}$, a substituted or unsubstituted heteroalkyl group of $C_1$-$C_{20}$, a hydroxy group, an amino group, a cyano group, a substituted or unsubstituted alkenyl group of $C_2$-$C_{20}$, a substituted or unsubstituted alkoxy group of $C_1$-$C_{20}$, a substituted or unsubstituted alkylsulfonamide group of $C_1$-$C_{20}$, a substituted or unsubstituted arylsulfonamide group of $C_6$-$C_{20}$, a substituted or unsubstituted acylamino group of $C_1$-$C_{20}$, an alkylureido group of $C_1$-$C_{20}$, an arylureido group of $C_6$-$C_{20}$, an alkoxycarbonyl group of $C_2$-$C_{20}$, an alkoxycarbonylamino group of $C_2$-$C_{20}$, a carbamoyl group, a sulfamoyl group, a sulfo group or its salt, a carboxyl group or its salt, a substituted or unsubstituted hydroxyalkyloxyalkyl group of $C_1$-$C_{20}$, a substituted or unsubstituted dialkylaminoalkyl group of $C_1$-$C_{20}$, a substituted or unsubstituted pyridylalkyl group of $C_6$-$C_{20}$, a substituted or unsubstituted pyridyl group of $C_5$-$C_{20}$, a substituted or unsubstituted imidazolyl group of $C_6$-$C_{20}$, a hydrazine group, a hydrazone group, a substituted or unsubstituted pyridylalkyl group of $C_1$-$C_{20}$, a substituted or unsubstituted aryl group of $C_6$-$C_{20}$, a substituted or unsubstituted arylalkyl group of $C_6$-$C_{20}$, a substituted or unsubstituted heteroaryl group of $C_6$-$C_{20}$, a heteroarylalkyl group of $C_6$-$C_{20}$, a substituted or unsubstituted heteroarylalkenyl group of $C_6$-$C_{20}$, and a substituted or unsubstituted heterocycloalkyl group of $C_3$-$C_{20}$;

$R_5$ and $R_6$ are each independently a hydrophilic mono-substituent or a same or different hydrophilic multi-substituent;

M is a metal atom selected from Groups III through XIV other than ruthenium (Ru) or copper (I);

X is an anionic moiety;

Y is a neutral moiety;

Z is a counterion;

o, p, and q are each independently an integer of 0 to 10, wherein a sum of o and p is not equal to zero, wherein X has a negative charge of −1 to −6 and is one or more selected from the group consisting of —R"C(=O)—O*, —R"CN*, —R"OO*, —R"O*, —R"SCN*, —R"N₃*, —R"CO₃*, and —R"SO₄*, wherein the * represents the position at which the moiety X binds to the metal M and R" is one of an alkylene of $C_2$-$C_{20}$, an arylene of $C_6$-$C_{20}$, heteroarylene of $C_2$-$C_{20}$, and —(CH₂CH₂O)$_z$— where Z is 1 to 50.

2. The bipyridine-based metal complex of claim 1, wherein $R_5$ and $R_6$ are each independently selected from the group consisting of —OA, —R'OA, —R'COOA —COOA, —SO₂NH₂, —R'SO₂A, —PO₃H, —PO₃A, —SO₂NHCOR, —NH₂, and —NR₃, where R is an alkyl group of $C_1$-$C_{20}$, an aryl group of $C_6$-$C_{20}$, or a heteroaryl group of $C_2$-$C_{20}$, R' is an alkylene group of $C_2$-$C_{20}$, an arylene group of $C_6$-$C_{20}$, or a heteroarylene group of $C_2$-$C_{20}$, and A is one or more selected from the group consisting of a hydrogen atom, an alkaline metal, ammonium, a substituted or unsubstituted alkyl group of $C_1$-$C_{12}$, and an aryl group of $C_6$-$C_{20}$.

3. The bipyridine-based metal complex of claim 1, wherein M has a positive charge of +1 to +5, and is selected from the group consisting of silver (Ag), aluminum (Al), gold (Au), cerium (Ce), cobalt (Go), chromium (Cr), copper II (Cu II), europium (Eu), iron (Fe), germanium (Ge), indium (In), lanthanum (La), manganese (Mn), nickel (Ni), palladium (Pd), platinum (Pt), rhodium (Rd), scandium (Sc), silicon (Si), samarium (Sm), titanium (Ti), uranium (U), zinc (Zn), and zirconium (Zr).

4. The bipyridine-based metal complex of claim 1, wherein Y is one or more selected from the group consisting of triphenylphosphinyl, —R"—NH₂* where R" is one of an alkylene of $C_2$-$C_{20}$, an arylene of $C_6$-$C_{20}$, a heteroarylene of $C_2$-$C_{20}$, and —(CH₂CH₂O)$_z$—, where Z is 1 to 50, 2,2'-bipyridyl, 1,10-phenanthrolyl, 2,2',2'-terpyridyl, and ligands represented by the following structural Formulas:

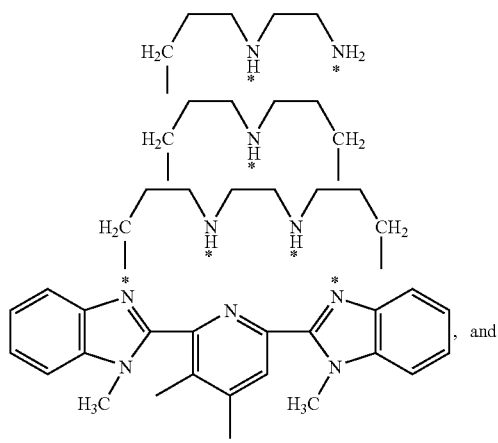

wherein the * represents a position at which the moiety Y binds to the metal M.

5. The bipyridine-based metal complex of claim 1, wherein the Z has a charge of –2 to 2, and is an anion selected from the group consisting of a halide ion, a sulfite ion, an alkylsulfite ion of $C_1$-$C_{10}$, a sulfate ion, an alkylsulfate ion of $C_1$-$C_{10}$, a nitrate ion, a nitrite ion a perchloric acid ion, a carboxylate ion of $C_1$-$C_{10}$, a salicylate ion, a benzoate ion, a hexafluorophosphate ion, and a tetrafluoroborate ion or a cation selected from the group consisting of a lithium ion, a sodium ion, a potassium ion, an ammonium ion, and a phosphonium ion.

6. A bipyridine-based metal complex represented by the following Formula II:

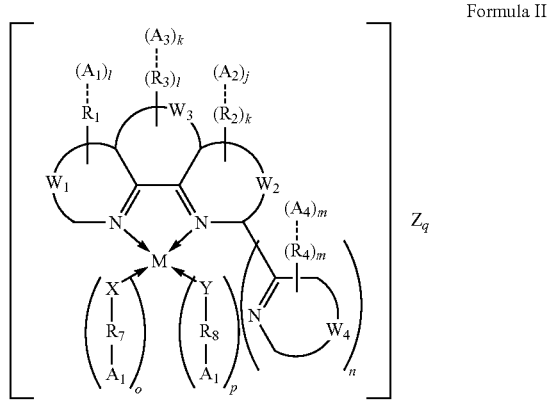

Formula II wherein $W_1$ and $W_2$ are each independently atoms required to form a 4- to 8-membered heteroaryl group or heterocycloalkenyl group, and $W_4$ is atoms required to form 4- to 8-membered heteroaryl groups or heterocycloalkenyl groups;

$W_3$ refers to atoms required to form one of 0- or 6-membered cycloalkyl group, a cycloalkenyl group, a heteroaryl group, a heterocycloalkenyl group, and a heterocycloalkenyl group;

n is an integer of 0 to 5;

$A_1$, $A_2$, $A_3$, and $A_4$ are each independently a same or different colorant and respectively bind with the ring compounds, $W_1$, $W_2$, $W_3$, and $W_4$;

i, j, k, and m are each independently 0 or 1, wherein a sum of i, j, k, and m is not equal to zero;

where all of i, j, k, and m are 1, $R_1$, $R_2$, $R_3$, and $R_4$ are each a linker;

where i is 0, $R_1$ is a mono-substituent or a same or different multi-substituent and is one of: a hydrogen atom, a halogen atom, a nitro group, —$SO_3H$, —COOH, a substituted or unsubstituted alkyl group of $C_1$-$C_{20}$, a substituted or unsubstituted heteroalkyl group of $C_1$-$C_{20}$, a hydroxy group, an amino group, a cyano group, a substituted or unsubstituted alkenyl group of $C_2$-$C_{20}$, a substituted or unsubstituted alkoxy group of $C_1$-$C_{20}$, a substituted or unsubstituted alkylsulfonamide group of $C_1$-$C_{20}$, a substituted or unsubstituted arylsulfonamide group of $C_6$-$C_{20}$, a substituted or unsubstituted acylamino group of $C_1$-$C_{20}$, an alkylureido group of $C_1$-$C_{20}$, an arylureido group of $C_6$-$C_{20}$, an alkoxycarbonyl group of $C_2$-$C_{20}$, an alkoxycarbonylamino group of $C_2$-$C_{20}$, a carbamoyl group, a sulfamoyl group, a sulfo group or its salt, a carboxyl group or its salt, a substituted or unsubstituted hydroxyalkyloxyalkyl group of $C_1$-$C_{20}$, a substituted or unsubstituted dialkylaminoalkyl group of $C_1$-$C_{20}$, a substituted or unsubstituted pyridylalkyl group of $C_6$-$C_{20}$, a substituted or unsubstituted pyridyl group of $C_5$-$C_{20}$, a substituted or unsubstituted imidazolyl group of $C_6$-$C_{20}$, a hydrazine group, a hydrazone group, a substituted or unsubstituted pyridylalkyl group of $C_1$-$C_{20}$, a substituted or unsubstituted aryl group of $C_6$-$C_{20}$, a substituted or unsubstituted arylalkyl group of $C_6$-$C_{20}$, a substituted or unsubstituted heteroaryl group of $C_6$-$C_{20}$, a heteroarylalkyl group of $C_6$-$C_{20}$, a substituted or unsubstituted heteroarylalkenyl group of $C_6$-$C_{20}$, and a substituted or unsubstituted heterocycloalkyl group of $C_3$-$C_{20}$;

where j is 0, $R_2$ is referred to in a description of $R_1$, where i is 0;

where k is 0, $R_3$ is referred to in a description of $R_1$ where i is 0;

where m is 0, $R_4$ is referred to in a description of $R_1$ where i is 0;

$R_7$ and $R_6$ are each independently a hydrophilic monosubstituent or a same or different hydrophilic multi-substituent;

M is a metal atom selected from Groups III through XIV;

X is an anionic ligand;

Y is a neutral ligand;

Z is a counterion;

o, p, and q are each independently an integer of 0 to 10, wherein a sum of o and p is not equal to zero.

7. The bipyridine-based metal complex of claim 6, wherein $R_7$ and $R_8$ are each independently selected from the group consisting of —CO—, —$SO_3A$-, and —$SO_2A$-, and A is one or more selected from the group consisting of, when $A_1$ is monovalent, a hydrogen atom, an alkaline metal, and ammonium, and consisting of a substituted or unsubstituted alkyl group of $C_1$-$C_{12}$, and an aryl group of $C_6$-$C_{20}$.

8. The bipyridine-based metal complex of claim 6, wherein the linker is selected from the group consisting of —O—, —C(=O)O—, —NH—, —C(=O)NH—, and —CH=N—.

9. The bipyridine-based metal complex of claim 6, wherein M has a positive charge of +1 to +5, and is selected from the group consisting of Ag, Al, Au, Ce, Co, Cr, Cu, Eu, Fe, Ge, In, La, Mn, Ni, Pd, Pt, Rd, Ru, Sc, Si, Sm, Ti, U, Zn, and Zr.

10. The bipyridine-based metal complex of claim 6, wherein X has a negative charge of –1 to –6, and is one or more selected from the group consisting of a halide ion, a hydroxy ion, a nitrate ion, a carboxylate ion of C1-C10, a cyano ion, a peroxy ion, an acetylacetonato ion and its derivative ion, a phenolate ion of salicylaldehyde and its derivative, a glycynato ion, a thiocyanate ion, an azide ion, a carbonate ion, an oxalate ion, and a sulfate ion.

11. The bipyridine-based metal complex of claim 6, wherein Y is one or more selected from the group consisting of triphenylphosphinyl, —R"NH$_2$* where R" is alkylene of $C_2$-$C_{20}$, arylene of $C_6$-$C_{20}$, or heteroarylene of $C_2$-$C_{20}$, 2,2'-bipyridyl, 1,10-phenanthrolyl, 2,2',2"-terpyridyl, and ligands represented by the following structural Formulas:

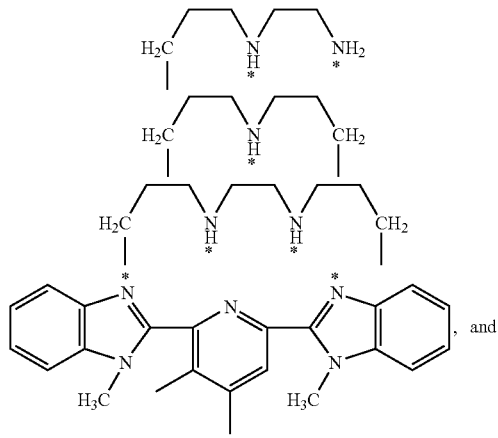

, and wherein the * represents a position at which the moiety Y binds to the metal M.

12. The bipyridine-based metal complex of claim 6, wherein Z has a charge of −2 to 2, and is an anion selected from the group consisting of a halide ion, a sulfite ion, an alkylsulfite ion of $C_1$-$C_{10}$, a sulfate ion, an alkylsulfate ion of $C_1$-$C_{10}$, a nitrate ion, a nitrite ion, a perchloric acid ion, a carboxylate ion of $C_1$-$C_{10}$, a salicylate ion, a benzoate ion, a hexafluorophosphate ion, and a tetrafluoroborate ion or a cation selected from the group consisting of a lithium ion, a sodium ion, a potassium ion, an ammonium ion, and a phosphonium ion.

13. An ink composition comprising the bipyridine-based metal complex of claim 1 and an aqueous liquid medium.

14. The ink composition of claim 13, wherein the bipyridine-based metal complex is used in an amount of 0.1 to 10 parts by weight, based on 100 parts by weight of the aqueous liquid medium.

15. The ink composition of claim 14, wherein the aqueous medium comprises one of water and water with at least one organic solvent.

16. An ink composition comprising the bipyridine-based metal complex of claim 6 and an aqueous liquid medium.

17. The ink composition of claim 16, wherein the bipyridine-based metal complex is used in an amount of 0.1 to 10 parts by weight, based on 100 parts by weight of the aqueous liquid medium.

18. The ink composition of claim 16, wherein the aqueous medium comprises one of water and water with at least one organic solvent.

19. The bipyridine-based metal complex of claim 11, wherein $A_1$, $A_2$, $A_3$ and $A_4$ are each independently selected from the group consisting of C.I. DIRECT BLACK 9, 17, 19, 22, 32, 56, 91, 94, 97, 166, 168, 174, and 199; C.I. DIRECT BLUE 1, 10, 15, 22, 77, 78, 80, 200, 201, 202, 203, 207, and 211; C.I. DIRECT RED 2, 4, 9, 23, 31, 39, 63, 72, 83, 84, 89, 111, 173, 184, and 240; C.I. DIRECT YELLOW 8, 9, 11, 12, 27, 28, 29, 33, 35, 39, 41, 44, 50, 53, and 58; a carbon black, graphite, a vitreous carbon, an activated charcoal, an activated carbon, anthraquinone, a phthalocyanine blue, a phthalocyanine green, diazos, monoazos, pyranthrones, perylene, quinacridone, and indigoid pigments.

20. An ink composition comprising an aqueous liquid medium, a colorant and at least one of a bipyridine-based metal complex represented by the following Formula I and a bipyridine-based metal complex represented by the following Formula II:

Formula I:

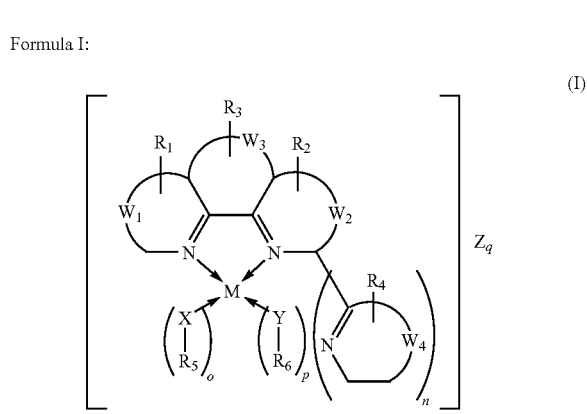

wherein $W_1$ and $W_2$ are each independently atoms required to form a 4- to 8-membered heteroaryl group or heterocycloalkenyl group, and $W_4$ is atoms required to form 4- to 8-membered heteroaryl groups or heterocycloalkenyl groups;

$W_3$ refers to atoms required to form one of a 0 or 6-membered cycloalkyl group, a cycloalkenyl group, an aryl group, a heteroaryl group, a heterocycloalkyl group, and a heterocycloalkenyl group;

n is an integer of 0 to 5;

$R_1$, $R_2$, $R_3$, and R4 are mono-substituents or a same or different multi-substituents, and are each independently one of a hydrogen atom, a halogen atom, a nitro group, —SO$_3$H, —COOH, a substituted or unsubstituted alkyl group of $C_1$-$C_{20}$, a substituted or unsubstituted heteroalkyl group of $C_1$-$C_{20}$, a hydroxy group, an amino group, a cyano group, a substituted or unsubstituted alkenyl group of $C_2$-$C_{20}$, a substituted or unsubstituted alkoxy group of $C_1$-$C_{20}$, a substituted or unsubstituted alkylsulfonamide group of $C_1$-$C_{20}$, a substituted or unsubstituted arylsulfonamide group of $C_6$-$C_{20}$, a substituted or unsubstituted acylamino group of $C_1$-$C_{20}$, an alkylureido group of $C_1$-$C_{20}$, an arylureido group of $C_6$-$C_{20}$, an alkoxycarbonyl group of $C_2$-$C_{20}$, an alkoxycarbonylamino group of $C_2$-$C_{20}$, a carbamoyl group, a sulfamoyl group, a sulfo group or its salt, a carboxyl group or its salt, a substituted or unsubstituted hydroxyalkyloxyalkyl group of $C_1$-$C_{20}$, a substituted or unsubstituted dialkylaminoalkyl group of $C_1$-$C_{20}$, a substituted or unsubstituted pyridylalkyl group of $C_6$-$C_{20}$, a substituted or unsubstituted pyridyl group of $C_5$-$C_{20}$, a substituted or unsubstituted imidazolyl group of $C_6$-$C_{20}$, a hydrazine group, a hydrazone group, a substituted or unsubstituted pyridylalkyl group of $C_1$-$C_{20}$, a substituted or unsubstituted aryl group of $C_6$-$C_{20}$, a substituted or unsubstituted arylalkyl group of $C_6$-$C_{20}$, a substituted or unsubstituted heteroaryl group of $C_6$-$C_{20}$, a heteroarylalkyl group of $C_6$-$C_{20}$, a substituted or unsubstituted heteroarylalkenyl group of $C_6$-$C_{20}$, and a substituted or unsubstituted heterocycloalkyl group of $C_3$-$C_{20}$;

$R_7$ and $R_8$ are each independently a hydrophilic mono-substituent or a same or different hydrophilic multi-substituent;

M is a metal atom selected from Groups III through XIV;

X is an anionic moiety;

Y is a neutral moiety;

Z is a counterion;

o, p, and q are each independently an integer of 0 to 10, wherein a sum of o and p is not equal to zero; and Formula II:

Formula II

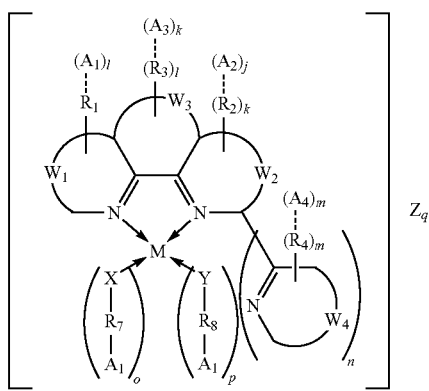

wherein $A_1$, $A_2$, $A_3$, and $A_4$ are each independently a same or different colorant and respectively bind with the ring compounds, $W_1$, $W_2$, $W_3$, and $W_4$;

i, j, k, and m are each independently 0 or 1, wherein a sum of i, j, k, and m is not equal to zero;

where all of i, j, k, and m are 1, $R_1$, $R_2$, $R_3$, and $R_4$ are each a linker;

where i is 0, $R_1$ is a mono-substituent or a same or different multi-substituent and is one of: a hydrogen atom, a halogen atom, a nitro group, —$SO_3H$, —COOH, a substituted or unsubstituted alkyl group of $C_1$-$C_{20}$, a substituted or unsubstituted heteroalkyl group of $C_1$-$C_{20}$, a hydroxy group, an amino group, a cyano group, a substituted or unsubstituted alkenyl group of $C_2$-$C_{20}$, a substituted or unsubstituted alkoxy group of $C_1$-$C_{20}$, a substituted or unsubstituted alkylsulfonamide group of $C_1$-$C_{20}$, a substituted or unsubstituted arylsulfonamide group of $C_6$-$C_{20}$, a substituted or unsubstituted acylamino group of $C_1$-$C_{20}$, an alkylureido group of $C_1$-$C_{20}$, an arylureido group of $C_6$-$C_{20}$, an alkoxycarbonyl group of $C_2$-$C_{20}$, an alkoxycarbonylamino group of $C_2$-$C_{20}$, a carbamoyl group, a sulfamoyl group, a sulfo group or its salt, a carboxyl group or its salt, a substituted or unsubstituted hydroxyalkyloxyalkyl group of $C_1$-$C_{20}$, a substituted or unsubstituted dialkylaminoalkyl group of $C_1$-$C_{20}$, a substituted or unsubstituted pyridylalkyl group of $C_6$-$C_{20}$, a substituted or unsubstituted pyridyl group of $C_5$-$C_{20}$, a substituted or unsubstituted imidazolyl group of $C_6$-$C_{20}$, a hydrazine group, a hydrazone group, a substituted or unsubstituted pyridylalkyl group of $C_1$-$C_{20}$, a substituted or unsubstituted aryl group of $C_6$-$C_{20}$, a substituted or unsubstituted arylalkyl group of $C_6$-$C_{20}$, a substituted or unsubstituted heteroaryl group of $C_6$-$C_{20}$, a heteroarylalkyl group of $C_6$-$C_{20}$, a substituted or unsubstituted heteroarylalkenyl group of $C_6$-$C_{20}$, and a substituted or unsubstituted heterocycloalkyl group of $C_3$-$C_{20}$;

where j is 0, $R_2$ is referred to in a description of $R_1$ where i is 0;

where k is 0, $R_3$ is referred to in a description of $R_1$ where i is 0;

where m is 0, $R_4$ is referred to in a description of $R_1$ where i is 0.

21. The ink composition of claim 20, further including at least one additive selected from the group consisting of a viscosity modifier, a surfactant, a metal oxide, a welling agent, and a storage stabilizer, wherein an amount of the additive/additives comprises an amount of 0.5 to 30 parts by weight, based on 100 parts by weight of the colorant.

* * * * *

UNITED STATES PATENT AND TRADEMARK OFFICE
CERTIFICATE OF CORRECTION

PATENT NO.        : 7,718,803 B2
APPLICATION NO.   : 10/896029
DATED             : May 18, 2010
INVENTOR(S)       : Jong-in Lee et al.

It is certified that error appears in the above-identified patent and that said Letters Patent is hereby corrected as shown below:

Column 20, Line 55 change "(Go)" to --(Co)--

Column 20, Line 66 change "2,2'2'-terpyridyl," to --2,2'2"-terpyridyl,--

Column 21, Line 27 change "ion" to --ion,--

Column 22, Line 33 change "R1," to --R1--

Column 22, Line 39 change "R6" to --R8--

Column 23, Line 59 change "claim 11," to --claim 6,--

Column 26, Line 36 change "welling" to --wetting--

Signed and Sealed this

Seventh Day of September, 2010

David J. Kappos
*Director of the United States Patent and Trademark Office*